United States Patent
Hickenboth et al.

(10) Patent No.: US 8,563,560 B2
(45) Date of Patent: *Oct. 22, 2013

(54) PREPARATION OF BICYCLIC GUANIDINE SALTS IN AN AQUEOUS MEDIA

(75) Inventors: Charles R. Hickenboth, Cranberry Township, PA (US); Christopher A. Dacko, Pittsburgh, PA (US); Steven R. Zawacky, Pittsburgh, PA (US); Gregory J. McCollum, Gibsonia, PA (US)

(73) Assignee: PPG Industries Ohio, Inc., Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/035,048

(22) Filed: Feb. 25, 2011

(65) Prior Publication Data

US 2012/0220770 A1 Aug. 30, 2012

(51) Int. Cl.
*A01N 43/90* (2006.01)
*A61K 31/519* (2006.01)
*C07D 487/00* (2006.01)

(52) U.S. Cl.
USPC .......................... 514/259.1; 544/279

(58) Field of Classification Search
None
See application file for complete search history.

(56) References Cited

U.S. PATENT DOCUMENTS

| | | | |
|---|---|---|---|
| 2,473,111 A | 6/1949 | Short et al. | |
| 3,724,386 A | 4/1973 | Schmidt | |
| 3,769,288 A | 10/1973 | Stahle et al. | |
| 3,828,122 A | 8/1974 | McPhee et al. | |
| 3,909,200 A | 9/1975 | Redmore | |
| 4,297,255 A | 10/1981 | Schenck | |
| 4,663,472 A | 5/1987 | Green | |
| 4,757,116 A | 7/1988 | Greco | |
| 4,797,487 A | 1/1989 | A'Court | |
| 4,869,772 A | 9/1989 | McDonnell | |
| 4,874,822 A | 10/1989 | Rasmussen | |
| 5,268,473 A | 12/1993 | Moren | |
| 5,506,279 A | 4/1996 | Babu | |
| 5,659,011 A | 8/1997 | Waldmann | |
| 5,998,013 A | 12/1999 | Shoshi | |
| 6,057,034 A | 5/2000 | Yamazaki | |
| 6,075,065 A | 6/2000 | Yamazaki | |
| 6,245,922 B1 | 6/2001 | Heilmann | |
| 6,506,858 B1 | 1/2003 | Knuuttila | |
| 6,617,399 B2 | 9/2003 | Konarski | |
| 6,635,690 B2 | 10/2003 | Heilmann | |
| 6,743,921 B2 | 6/2004 | Tucker | |
| 6,852,193 B2 | 2/2005 | Kneafsey | |
| 6,894,082 B2 | 5/2005 | Brantl | |
| 6,936,641 B2 | 8/2005 | Molock | |
| 7,012,120 B2 | 3/2006 | Klenarczk | |
| 7,015,286 B2 | 3/2006 | Heilmann | |
| 7,074,858 B2 | 7/2006 | Heilmann | |
| 7,211,616 B2 | 5/2007 | Kaszubski | |
| 7,384,984 B2 | 6/2008 | Lewandowski | |
| 8,148,490 B2 * | 4/2012 | McCollum et al. | 528/405 |
| 2003/0061825 A1 | 4/2003 | Sullivan | |
| 2003/0092694 A1 | 5/2003 | Nilsson | |
| 2003/0164222 A1 | 9/2003 | Kneafsey | |
| 2003/0181318 A1 | 9/2003 | Tucker | |
| 2004/0059044 A1 | 3/2004 | Olson | |
| 2004/0063848 A1 | 4/2004 | Olson | |
| 2005/0182148 A1 | 8/2005 | Gaud | |
| 2005/0211580 A1 | 9/2005 | Kaszubski | |
| 2005/0288457 A1 | 12/2005 | Liu | |
| 2005/0288458 A1 | 12/2005 | Klemarczyk | |
| 2006/0004119 A1 | 1/2006 | Molock | |
| 2006/0046068 A1 | 3/2006 | Barancyk | |
| 2006/0068198 A1 | 3/2006 | Bratys | |
| 2006/0158001 A1 | 7/2006 | Emch | |
| 2007/0048445 A1 | 3/2007 | DiMario | |
| 2007/0048504 A1 | 3/2007 | DiMario | |
| 2009/0042060 A1 | 2/2009 | Zawacky et al. | |
| 2009/0171025 A1 | 7/2009 | Matsushita | |
| 2009/0281313 A1 | 11/2009 | Minch | |
| 2009/0281314 A1 | 11/2009 | Boyd | |
| 2009/0286978 A1 | 11/2009 | Minch | |

FOREIGN PATENT DOCUMENTS

| | | |
|---|---|---|
| DE | 102006056311 A1 | 6/2008 |
| EP | 0152240 | 1/1985 |
| EP | 0198680 | 10/1986 |
| EP | 0295930 | 6/1988 |
| EP | 0380178 | 1/1990 |
| EP | 0449488 | 3/1991 |
| EP | 0554023 | 8/1993 |
| EP | 0837844 | 7/1996 |
| EP | 0874012 | 4/1998 |
| EP | 1401976 | 4/2002 |
| EP | 1788035 | 8/2005 |

(Continued)

OTHER PUBLICATIONS

Schmidtchen, "Synthese Symmetrisch Substituierter Bycyclischer Guanidine", Chemische Berichte, vol. 113, No. 6, 1980 (pp. 2175-2182).

Antonio Echavarren et al., "Anion-Receptor Molecules: Synthesis of a Chiral and Functionalized Binding Subunit, a Bicyclic Guanidinium Group Derived from L- or D-Asparagine", Helvetica Chimica Acta, vol. 71, No. 4, 1988 (pp. 685-693).

(Continued)

*Primary Examiner* — Jeffrey Murray
(74) *Attorney, Agent, or Firm* — Alicia M. Passerin

(57) ABSTRACT

Disclosed herein are bicyclic guanidine salts, useful as cure catalysts for electrodeposited coatings. The bicyclic guanidine salts are formed as the reaction product of reactants comprising (a) a compound having the general formula $CX_n$, wherein X is N, O, or S and wherein n is 2 to 4; (b) an acid; (c) dipropylene triamine; and (d) water, and an associated method for forming a bicyclic guanidine salt from the same reaction ingredients.

24 Claims, No Drawings

(56) References Cited

FOREIGN PATENT DOCUMENTS

| | | |
|---|---|---|
| GB | 1496111 | 12/1977 |
| JP | 02189330 | 7/1990 |
| JP | 10265612 | 10/1998 |
| JP | 11021352 | 1/1999 |
| JP | 2002273280 | 10/2000 |
| JP | 2006199721 | 3/2006 |
| WO | 2009027186 A2 | 3/2009 |
| WO | 2009137728 | 11/2009 |
| WO | 2011079041 A1 | 6/2011 |

OTHER PUBLICATIONS

Eusebio Juaristi et al., "Synthesis of New Chiral Derivative of N, N'-Dimethylpropyleneurea (DMPU) and Examination . . . ", Helvetica Chimica ACTA, vol. 85, No. 7 2002 (pp. 1999-2007).

Zhengqing You et al., "New AZT Conjugates as Potent Anit-HIV Agents", Nucleosides, Nucleotides and Nucleic Acids, vol. 25, No. 1, 2006 (pp. 37-54).

Cotton et al., "Homologues of the Easily Ionized Compound Mo2(hpp)4 Containing Smaller Bicyclic Guanidinates", Inorganic Chemistry, vol. 45, No. 14, 2006 (pp. 5493-5500).

Chong Han et al., "Synthesis of Carbamates and Ureas Using Zr(IV)-Catalyzed Exchange Processes", Organic Letters, vol. 9, No. 8, 2007 (pp. 1517-1520).

Dovlatyan et al., "Reactions of Derivatives of Amino- and Mercapto-sym-Triazines with Ethyleneimine and Ethylenediamine", Chemistry of Heterocyclic Compounds, 1993, vol. 29, Issue 6, pp. 704-707.

Shestakov et al., "Reaction of Cyanamides with N,N-Binucleophiles", Russian Journal of General Chemistry, 2006, vol. 76, No. 20, pp. 1647-1652.

* cited by examiner

PREPARATION OF BICYCLIC GUANIDINE SALTS IN AN AQUEOUS MEDIA

FIELD OF THE INVENTION

The present invention relates to methods for preparing bicyclic guanidine compounds, and more particularly to methods for preparing bicyclic guanidine salts in an aqueous media.

BACKGROUND INFORMATION

Dialkyltin oxides have traditionally been used as cure catalysts for electrodeposition coatings. Dialkyltin oxides, however, have been subjected to a number of regulatory restrictions by various countries due to environmental concerns. Therefore, bismuth has been used with increased frequency as the cure catalyst for electrodeposition coatings in lieu of dialkyltin oxide. There are, however, a number of shortcomings associated with using bismuth as the cure catalyst. For example, bismuth is often a less effective catalyst for various electrodeposition compositions when compared to dialkyltin oxide. Moreover, there may be cost and availability issues associated with using bismuth as a cure catalyst in the future. Accordingly, there is a need for an alternative catalyst for use in an electrodeposition coating. Moreover, there is also a need for an electrodeposition coating that is substantially free of tin.

One material being evaluated for use in electrodeposition coatings as a possible replacement for metal catalysts is cyclic guanidines such as bicyclic guanidines and bicyclic guanidine salts. Conventionally, bicyclic guanidines and bicyclic guanidine salts may be prepared in a variety of ways, but most known methods require high temperatures and long reaction times, or expensive and toxic reagents, or both. Ideally, it would be highly desirable to find a low cost, relatively safe, and efficient method for producing bicyclic guanidines and/or bicyclic guanidine salts.

SUMMARY OF THE INVENTION

One exemplary embodiment of the present invention discloses a bicyclic guanidine salt formed as the reaction product of reactants comprising (a) a compound having the general formula $CX_n$, wherein X is N, O, or S and wherein n is 2 to 4; (b) an acid; (c) dipropylene triamine; and (d) water.

Another exemplary embodiment discloses a method for forming a bicyclic guanidine salt comprising: (a) mixing water with a compound having the general formula $CX_n$, wherein X is N, O, or S and wherein n is 2 to 4; (b) adding an acid to (a); (c) exotherming (b) under agitation; (d) adding dipropylene triamine to (c); and (e) warming (d) to a reflux temperature.

Other related exemplary embodiments disclose multi-component composite coatings, coated substrates, and methods for coating a substrate.

DETAILED DESCRIPTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

As previously mentioned, the present invention is directed to methods for producing bicyclic guanidine ("BCG") salts; these methods may be lower cost, more efficient, and/or safer than current methods. In certain embodiments, the new methods can be carried out without the use of high temperatures and long reaction times. In addition, in certain embodiments, the new methods do not utilize expensive and toxic reagents.

In one embodiment, bicyclic guanidine salts may be formed via a guanidine exchange route. More specifically, as illustrated below, dipropylene triamine (DPTA) is combined, in the presence of water and acid (HA), with a molecule containing a highly electrophilic carbon, whose valences are satisfied by strongly electronegative atoms ($CX_n$), wherein X is N, O or S and wherein n is 2-4. This reaction produces the acid salt of 1,5,7-triazabicyclo[4.4.0]dec-5-ene in water, along with the corresponding byproduct $Z(H_mX)$, wherein m is 1-3 and Z is 1-6.

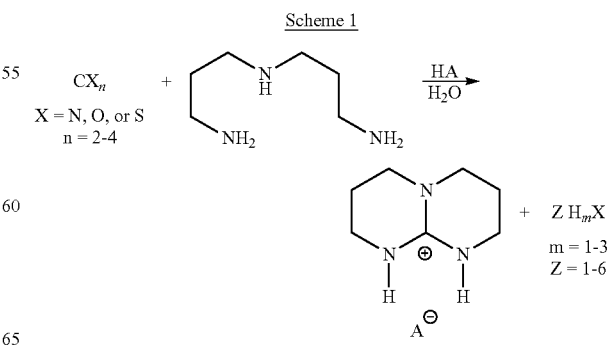

Scheme 1

The acid salt of 1,5,7-triazabicyclo[4.4.0]dec-5-ene may then further react with water to form a monocyclic urea as illustrated in the following reaction:

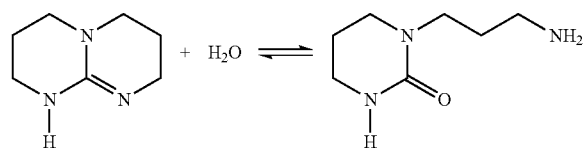

Exemplary molecules $CX_n$ that may be utilized in the embodiments of the present invention include, for example, one or more of guanidine carbonate salts (shown as (1) in Schemes 2 and 3 below), dicyandiamide (shown as (5) in Scheme 4 below), cyanamide, carbon disulfide, propylene carbonate, alkylorthoformates, and 1,1'-thiocarbonyl diimidazole (TCDI), as shown below:

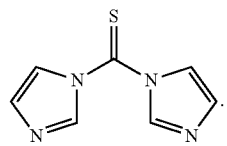 [SMILES: S=C(n1ccnc1)n1ccnc1]

Exemplary acids (HA) that may be used include, for example, hydrochloric acid, hydrobromic acid, hydroiodic acid, perchloric acid, sulfuric acid, nitric acid, phosphoric acid, boric acid, chromic acid, methanesulfonic acid, p-toluenesulfonic acid, trifluoromethanesulfonic acid, acetic acid, formic acid, citric acid, lactic acid, oxalic acid and combinations thereof.

In another more specific exemplary embodiment, as shown in Scheme 2 and Example 1 below, a guanidine carbonate salt (1) is dissolved in water and reacted with methanesulfonic acid, followed by addition of dipropylene triamine (2). The resulting solution is warmed to reflux and stirred for 16-24 hours to yield the methanesulfonic acid salt of 1,5,7-triazabicyclo[4.4.0]dec-5-ene (3) in water, as shown below:

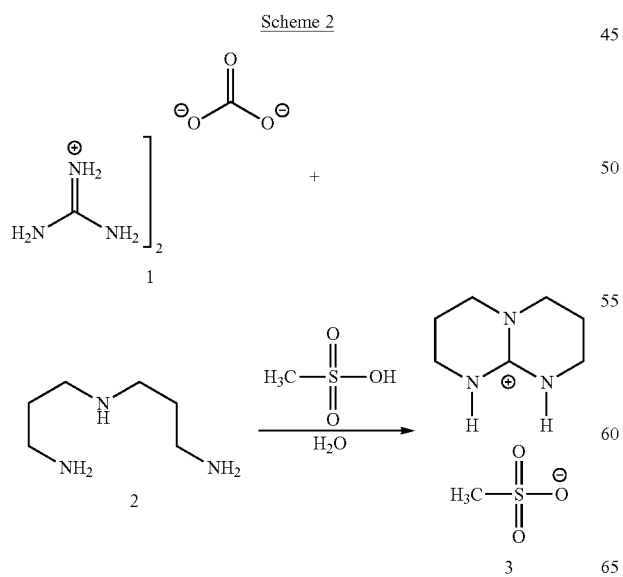

In still another specific exemplary embodiment, as shown in Scheme 3 and Example 2 below, a guanidine carbonate salt (1) is dissolved in water and reacted with hydrochloric acid, followed by addition of dipropylene triamine (2). The resulting solution is warmed to reflux and stirred for 4-6 hours to yield the chloride salt of 1,5,7-triazabicyclo[4.4.0]dec-5-ene (4) in water, as shown below:

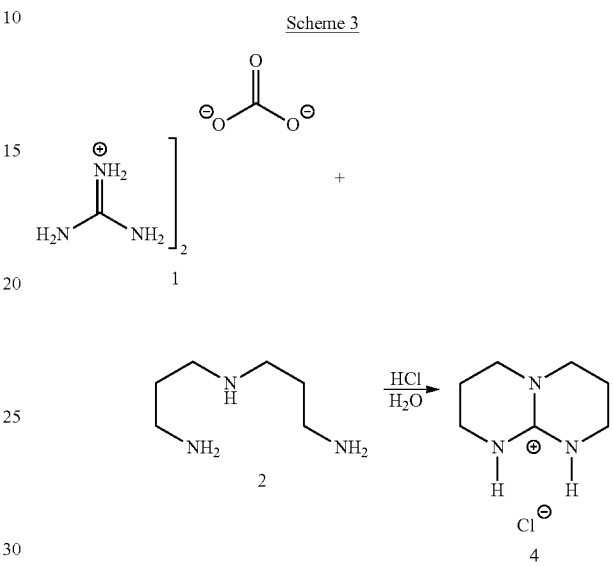

In yet another specific exemplary embodiment, as shown in Scheme 4 and Example 3 below, dicyandiamide (5) is dissolved in water and reacted with methanesulfonic acid, followed by addition of dipropylene triamine (2). The resulting solution is warmed to reflux and stirred for 2-4 hours to yield the methanesulfonic acid salt of 1,5,7-triazabicyclo[4.4.0]dec-5-ene (3) in water, as shown below:

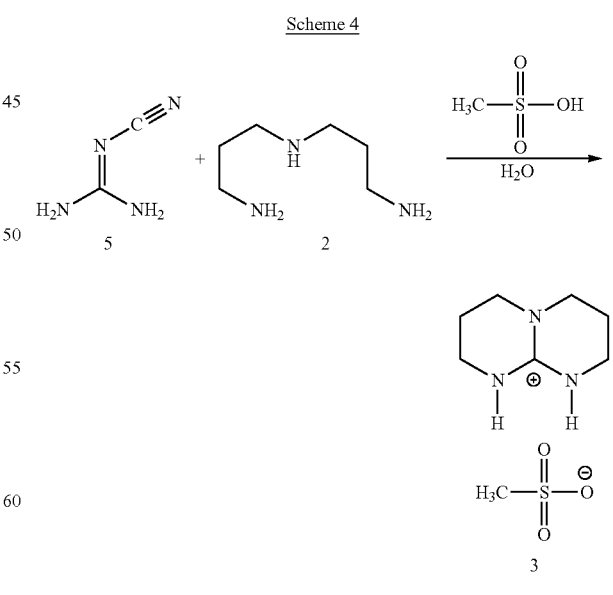

The present invention thus provides a low cost, relatively safe, and/or efficient method for producing bicyclic guanidine salts that are available for use in a wide variety of coat-

Example 1

Cyclic Guanidine-Methanesulfonic Acid Salt in Water

| # | Material | parts |
|---|---|---|
| 1 | Guanidine carbonate | 22.5 |
| 2 | Methanesulfonic acid | 24 |
| 3 | DI water | 46.5 |
| 4 | Dipropylene triamine | 32.8 |

Materials 1 and 3 were added to a round bottom flask equipped with a mechanical stirrer, reflux condenser, temperature probe and inert gas inlet. Material 2 was then added dropwise, and the mixture exothermed to 50° C. After further stirring for 8 minutes, material 4 was added all at once. A second exotherm occurred. After briefly stirring at ambient temperature, the mixture was warmed to reflux and the reaction progress was followed by $^{13}$C NMR. The reaction proceeds as illustrated in Scheme 2 above. After 18.5 hours, $^{13}$C NMR analysis suggested approximately 80% conversion of dipropylene triamine to the methanesulfonic acid salt of 1,5,7-triazabicyclo[4.4.0]dec-5-ene.

Example 2

Demonstrating the Use of Hydrochloric Acid as the Acid

| # | Material | parts |
|---|---|---|
| 1 | Guanidine carbonate | 54.6 |
| 2 | Concentrated hydrochloric acid | 83.33 |
| 3 | DI water | 138 |
| 4 | Dipropylene triamine | 170.6 |

Materials 1 and 3 were added to a round bottom flask equipped with a mechanical stirrer, reflux condenser, temperature probe and inert gas inlet. Material 2 was then added dropwise, and the mixture exothermed to 61° C. After further stirring for 5 minutes, material 4 was added all at once, and the reaction exothermed to 97° C. The mixture was then warmed to reflux and the reaction progress was followed by $^{13}$C NMR. The reaction proceeds as illustrated in Scheme 3 above. After about 4 hours, $^{13}$C NMR analysis suggested approximately 40% conversion of dipropylene triamine to the hydrochloric acid salt of 1,5,7-triazabicyclo[4.4.0]dec-5-ene.

Example 3

Demonstrating the Use of Dicyandiamide as the Carbon Source

| # | Material | parts |
|---|---|---|
| 1 | dicyandiamide | 42 |
| 2 | methanesulfonic acid | 96.1 |
| 3 | DI water | 138 |
| 4 | Dipropylene triamine | 131.2 |

Materials 1 and 3 were added to a round bottom flask equipped with a mechanical stirrer, reflux condenser, temperature probe and inert gas inlet. Material 2 was then added dropwise, and the mixture exothermed to 98° C. After further stirring for 100 minutes, material 4 was added over 25 minutes, and the reaction exothermed to 67° C. The mixture was then warmed to reflux and the reaction progress was followed by $^{13}$C NMR. The reaction proceeds as illustrated in Scheme 4 above. After about 155 minutes, $^{13}$C NMR analysis suggested the mixture contained approximately 32% conversion of dipropylene triamine to the methanesulfonic acid salt of 1,5,7-triazabicyclo[4.4.0]dec-5-ene along with an unidentified product.

Whereas particular embodiments of the invention have been described hereinabove for purposes of illustration, it will be evident to those skilled in the art that numerous variations of the details of the present invention may be made without departing from the invention as defined in the appended claims.

We claim:

1. A bicyclic guanidine salt formed as the reaction product of reactants comprising:
   (a) a compound having the general formula $CX_n$, wherein X is N, O, or S and wherein n is 2 to 4;
   (b) an acid;
   (c) dipropylene triamine; and
   (d) water,
   wherein the bicyclic guanidine salt reaction product formed is

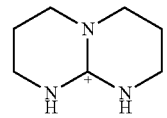

acid $\ominus$.

2. The bicyclic guanidine salt of claim 1, wherein the compound comprises one or more of a guanidine carbonate salt, dicyandiamide, cyanamide, carbon disulfide, propylene carbonate, alkylorthoformates, and 1,1'-thiocarbonyl diimidazole.

3. The bicyclic guanidine salt of claim 1, wherein the acid comprises hydrochloric acid, hydrobromic acid, hydroiodic acid, perchloric acid, sulfuric acid, nitric acid, phosphoric acid, boric acid, chromic acid, methanesulfonic acid, p-toluenesulfonic acid, trifluoromethanesulfonic acid, acetic acid, formic acid, citric acid, lactic acid, oxalic acid, and combinations thereof.

4. The bicyclic guanidine salt of claim 1, wherein the compound comprises a guanidine carbonate salt and wherein the acid comprises methanesulfonic acid.

5. The bicyclic guanidine salt of claim 1, wherein the compound comprises a guanidine carbonate salt and wherein the acid comprises hydrochloric acid.

6. The bicyclic guanidine salt of claim 1, wherein the compound comprises a dicyandiamide and wherein the acid comprises methanesulfonic acid.

7. The bicyclic guanidine salt of claim 1, wherein the bicyclic guanidine salt reaction product formed comprises a methanesulfonic acid salt of 1,5,7-triazabicyclo[4.4.0]dec-5-ene.

8. The bicyclic guanidine salt of claim 1, wherein the bicyclic guanidine salt reaction product formed comprises a chloride salt of 1,5,7-triazabicyclo[4.4.0]dec-5-ene.

9. A method for forming the bicyclic guanidine salt of claim 1 comprising:
 (a) mixing water with the compound having the general formula $CX_n$, wherein X is N, O, or S and wherein n is 2 to 4;
 (b) adding the acid to (a);
 (c) exotherming (b) under agitation;
 (d) adding the dipropylene triamine to (c); and
 (e) warming (d) to a reflux temperature.

10. The method of claim 9, wherein the compound comprises one or more of a guanidine carbonate salt, dicyandiamide, cyanamide, carbon disulfide, propylene carbonate, alkylorthoformates, and 1,1'-thiocarbonyl diimidazole.

11. The method of claim 9, wherein the acid comprises hydrochloric acid, hydrobromic acid, hydroiodic acid, perchloric acid, sulfuric acid, nitric acid, phosphoric acid, boric acid, chromic acid, methanesulfonic acid, p-toluenesulfonic acid, trifluoromethanesulfonic acid, acetic acid, formic acid, citric acid, lactic acid, oxalic acid, and combinations thereof.

12. The method of claim 9, wherein the compound comprises a guanidine carbonate salt and wherein the acid comprises methanesulfonic acid.

13. The method of claim 9, wherein the compound comprises a guanidine carbonate salt and wherein the acid comprises hydrochloric acid.

14. The method of claim 9, wherein the compound comprises dicyandiamide and wherein the acid comprises methanesulfonic acid.

15. The method of claim 9, wherein the formed bicyclic guanidine salt comprises a methanesulfonic acid salt of 1,5,7-triazabicyclo[4.4.0]dec-5-ene.

16. The method of claim 9, wherein the formed bicyclic guanidine salt comprises a chloride salt of 1,5,7-triazabicyclo [4.4.0]dec-5-ene.

17. The method of claim 9, wherein the acid of step (b) is added dropwise.

18. A bicyclic guanidine salt formed as the reaction product of reactants comprising:
 (a) a compound having the general formula $CX_n$, wherein X is N, O, or S and wherein n is 2 to 4;
 (b) an acid comprising hydrochloric acid, hydrobromic acid, hydroiodic acid, perchloric acid, sulfuric acid, nitric acid, phosphoric acid, boric acid, chromic acid, methanesulfonic acid, p-toluenesulfonic acid, trifluoromethanesulfonic acid, acetic acid, formic acid, citric acid, lactic acid, oxalic acid, and combinations thereof;
 (c) dipropylene triamine; and
 (d) water,
wherein the bicyclic guanidine salt reaction product formed is

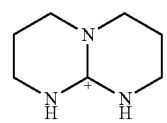

acid $\ominus$.

19. The bicyclic guanidine salt of claim 18, wherein the compound comprises one or more of a guanidine carbonate salt, dicyandiamide, cyanamide, carbon disulfide, propylene carbonate, alkylorthoformates, and 1,1'-thiocarbonyl diimidazole.

20. The bicyclic guanidine salt of claim 18, wherein the compound comprises a guanidine carbonate salt and wherein the acid comprises methanesulfonic acid.

21. The bicyclic guanidine salt of claim 18, wherein the compound comprises a guanidine carbonate salt and wherein the acid comprises hydrochloric acid.

22. The bicyclic guanidine salt of claim 18, wherein the compound comprises a dicyandiamide and wherein the acid comprises methanesulfonic acid.

23. The bicyclic guanidine salt of claim 18, wherein the bicyclic guanidine salt reaction product formed comprises a methanesulfonic acid salt of 1,5,7-triazabicyclo[4.4.0]dec-5-ene.

24. The bicyclic guanidine salt of claim 18, wherein the bicyclic guanidine salt reaction product formed comprises a chloride salt of 1,5,7-triazabicyclo[4.4.0]dec-5-ene.

* * * * *